(12) United States Patent
Kunert (10) Patent No.: US 8,428,885 B2
(45) Date of Patent: Apr. 23, 2013

(54) VIRTUAL SCREENING OF CHEMICAL SPACES

(75) Inventor: Lars Kunert, Laatzen (DE)

(73) Assignee: Lars Kunert, Laatzen (DE)

( * ) Notice: Subject to any disclaimer, the term of this patent is extended or adjusted under 35 U.S.C. 154(b) by 307 days.

(21) Appl. No.: 12/531,662

(22) PCT Filed: Mar. 19, 2008

(86) PCT No.: PCT/EP2008/053330
§ 371 (c)(1),
(2), (4) Date: Aug. 31, 2010

(87) PCT Pub. No.: WO2008/116811
PCT Pub. Date: Oct. 2, 2008

(65) Prior Publication Data
US 2010/0325141 A1    Dec. 23, 2010

Related U.S. Application Data

(60) Provisional application No. 60/919,741, filed on Mar. 23, 2007.

(30) Foreign Application Priority Data

Mar. 23, 2007  (EP) .................................... 07104765

(51) Int. Cl.
*G01N 33/50* (2006.01)
(52) U.S. Cl.
USPC .......................................................... 702/19
(58) Field of Classification Search .................. None
See application file for complete search history.

(56) References Cited

U.S. PATENT DOCUMENTS

2006/0036564 A1   2/2006   Yan et al.
2006/0224562 A1   10/2006  Yan et al.

OTHER PUBLICATIONS

Yan, et al, "Graph Indexing Based on Discriminative Frequent Structure Analysis," ACM Transactions on Database Systems, Dec. 2005, pp. 960-993, vol. 30, No. 4.
Irwin, et al, "Zinc—A Free Database of Commercially Available Compounds for Virtual Screening," J. Chem. Inf. Model, 2005, pp. 177-182, vol. 45, No. 1.
Hicks, et al., "Substructure Search Systems. 1. Performance Comparison of the MACCS, DARC, HTSS, CAS Registry MVSSS, and S4 Substructure Search Systems," J. Chem. Inf. Computer Science, 1990, pp. 191-199, vol. 30, No. 2.
Barnard, "Substructure Searching Methods: Old and New," J. Chem. Inf. Computer Science, 1993, pp. 532-538, vol. 33, No. 4.
Nagy, et al., "Substructure Search on Very Large Files Using Tree-Structured Databases, " Chemical Structures, The International Language of Chemistry, 1988, pp. 127-130, Springer-Verlag, Berlin, Germany.
Wipke, et al., "Tree-Structured Maximal Common Subgraph Searching. An Example of Parallel Computation with a Single Sequential Processor," Tetrahedron Computer Methodology, 1989, pp. 177-202, vol. 2, No. 3.
Shearer, et al, "Video Indexing and Similarity Retrieval by Largest Common Subgraph Detection Using Decision Trees," Pattern Recognition, 2001, pp. 1075-1091, vol. 34.
Borgelt, et al., "MoSS: A Program for Molecular Substructure Mining," Workshop Open Source Data Mining Software—2005, pp. 6-15.
Borgelt, "Combining Ring Extensions and Canonical Form Pruning," Workshop on Mining and Learning with Graphs, 2006.
McKay, "Practical Graph Isomorphism," Congressus Numerantium, 1981, pp. 45-87, vol. 30.
Rarey, et al., "Feature Trees: A New Molecular Similarity Measure Based on Tree Matching," Journal of Computer- Aided Molecular Design, 1998, pp. 471-490, vol. 12.
Cormen, et al., Introduction to Algorithms, 2000, chapter 37.3, pp. 974-978, McGraw-Hill.
Durant, et al., "Reoptimization of MDL Keys for Use in Drug Discovery," J. Chem. Inf. Computer Science, 2002, pp. 1273-1280, vol. 42, No. 6.
Garcia, et al., "Step-by-Step Calculation of All Maximum Common Substructures Through a Constraint Satisfaction Based Algorithm," J. Chem. Inf. Computer Science, 2004, pp. 30-41, vol. 44, No. 1.
Raymond, et al., "Maximum Common Subgraph Isomorphism Algorithms for the Matching of Chemical Structures," Journal of Computer-Aided Molecular Design, 2002, pp. 521-533, vol. 16.
Raymond, et al., "Heuristics for Similarity Searching of Chemical Graphs Using a Maximum Common Edge Subgraph Algorithm," J. Chem. Inf. Computer Science, 2002, pp. 305-316, vol. 42, No. 2.
Raymond, et al., "Effectiveness of Graph-based and Fingerprint-based Similarity Measures for Virtual Screening of 2D Chemical Structure Databases," Journal of Computer-Aided Molecular Design, 2002, pp. 59-71, vol. 16.
Raymond, et al., "RASCAL: Calculation of Graph Similarity using Maximum Common Edge Subgraphs," The Computer Journal, 2002, pp. 631-644, vol. 45, No. 6.
Messmer, et al., "A Decision Tree Approach to Graph and Subgraph Isomorphism Detection," Pattern Recognition, 1999, pp. 1979-1998, vol. 32.
Yan, et al., "Graph Indexing: A Frequent Structure-based Approach," SIGMOD 2004 Jun. 13-18, 2004, Paris, France.
X. Mdl. MDL drug data report (MDDR version 2006.1), 2006.

*Primary Examiner* — Jason Sims (57) ABSTRACT

The present invention relates to the screening of molecules, for example for candidates for the development of new drugs. In more detail, the invention relates to a method for searching molecules among a number of molecules to be screened that are similar to a given set of query molecules.

9 Claims, 12 Drawing Sheets

| activity class | #molecules | fold |
|---|---|---|
| Dehydropeptidase-1 Inhibitor | 12 | 1 |
| MAO Inhibitor | 22 | 1 |
| Phospholipase A4 Inhibitor | 67 | 1 |
| Carbonic Anhydrase Inhibitor | 77 | 1 |
| Acetylcholinesterase Inhibitor | 146 | 1 |
| Muscarinic (M1) Agonist | 694 | 1 |
| Dihydroorotase Inhibitor | 10 | 2 |
| GABA-B Receptor Antagonist | 18 | 2 |
| AMPA Receptor Antagonist | 63 | 2 |
| Histamine H3 Antagonist | 77 | 2 |
| Reverse Transcriptase Inhibitor | 129 | 2 |
| NMDA Receptor Antagonist | 488 | 2 |
| Mannosidase Inhibitor | 10 | 3 |
| Glutamate Release Inhibitor | 18 | 3 |
| MAO A Inhibitor | 40 | 3 |
| Poly (ADP-Ribose) Synthease Inhibitor | 74 | 3 |
| Sigma Antagonist | 126 | 3 |
| Lipoxygenase Inhibitor | 446 | 3 |
| 3-Hydroxyanthranilate Oxygenase Inhibitor | 14 | 4 |
| 5HT3 Agonist | 26 | 4 |
| Nicotinic Agonist | 71 | 4 |
| Aldose Reductase Inhibitor | 122 | 4 |
| Nitric Oxide Synthase Inhibitor | 228 | 4 |
| Transglutaminase (Factor XIIIA) Inhibitor | 13 | 5 |
| Histamine H3 Agonist | 24 | 5 |
| Dipeptidylaminopepidase VI Inhibitor | 67 | 5 |
| Tyrosine-specific Protein Kinase Inhibitor | 103 | 5 |
| 5HT Reuptake Inhibitor | 218 | 5 |

VIRTUAL SCREENING OF CHEMICAL SPACES

FIELD OF THE INVENTION

The present invention relates to the screening of molecules, for example for candidates for the development of new drugs. In more detail, the invention relates to a method for searching molecules among a number of molecules to be screened that are similar to a given set of query molecules.

BACKGROUND OF THE INVENTION

A frequently used approach for the development of new drugs is similarity-based screening. This approach does not depend on structural knowledge about the molecular target— the binding mode and the exact location of the interaction between the drug and the body of the patient. The knowledge of one drug (active molecule or compound) is sufficient. Starting from this single or a small set (<1000) of active molecules databases of small (druglike) molecules are screened for candidates for the development of new drugs. Publicly available databases contain between two and three million druglike molecules. Proprietary databases may contain a multiple of this number.

The screening can be done in a laboratory or (virtually) with a computer. In practice the virtual screening is done prior to lab-based screening for time and economical reasons. Established virtual screening methods use one-to-one comparisons between active molecules and the screened molecules. Simple bit-vector-based methods can calculate one million pairwise comparisons in one minute. More elaborate graph-based methods, which compute maximum common subgraphs or substructures or edit-distances need several hours for one million pairwise comparisons.

Fast virtual screening programs represent molecules by a vector of bits. Examples for these programs are MACCS Keys from MDL Information System Inc., BCI fingerprints from Barnard Chemical Information Ltd. and Daylight Fingerprints. The screening is done by bit-vector comparison. Each bit codes the absence or presence of one or a set of small molecular fragments within the represented molecule.

While the comparison of bit-vectors is very fast, the results are hard to interpret. The descriptor allows for high similarities between completely unrelated structures that share a set of common fragments. A maximum common subgraph based similarity measure, as applied in this invention, is highly specific. The reported matches can be easily visualized and interpreted. The measure can be relaxed in well-defined ways by using edit operations or by representing the compared molecules as reduced graphs.

Subgraph isomorphism based methods are used successfully for substructure searching in molecular databases (see M. G. Hicks and C. Jochum, J. Chem. Inf. Comput. Sci., 30:191-199, 1990; J. M. Barnard, J. Chem. Inf. Comput. Sci., 33:533-538, 1993). Here generally a two-step procedure is used: A fast bit-vector based screening (prefiltering) program identifies a course set of most similar molecules. Then a subgraph isomorphism program is applied to the reduced input set.

The main drawback of this approach for virtual screening is the absence of useful boundaries for the maximum common subgraph similarity given the result of the prefiltering program. This is acceptable for substructure searching where only exact matching subgraphs are desired and a high similarity threshold can be used for the prefiltering. In virtual screening, where maximum common subgraph based similarity values of 0.8 and below are desired, the prefiltering step becomes inefficient.

An interesting approach for substructure searching is used by the hierarchical tree substructure search program (HTSS) (see M. Z. Nagy, S. Kozics, T. Veszpremi, and P. Bruck, "Substructure search on very large files using tree-structured databases", in W. A. Warr, editor, "Chemical Structures. The International Language of Chemistry.", pages 127-130, Springer-Verlag, Berlin, Germany, 1988). This program precomputes a tree of expanding atomic neighborhoods. For each atom of the query molecule a path of exactly matching neighborhoods in the tree is traversed. A subgraph isomorphism match can be directly inferred from a matching set of atomic neighborhoods. A direct extension of this approach to the computation of maximum common subgraphs or edit-distances is not possible. Instead of exactly matching neighborhoods and a simple path traversal, approximate matches and a backtracking procedure would be necessary.

Wipke and Rogers introduced such an algorithm using a more general tree of subgraphs instead of atomic neighborhoods (see W. T. Wipke and D. Rogers, Tetrahedron Computer Methodology, 2:177-202, 1989). While the algorithm gives a good speedup compared to the computation of maximum common subgraphs between the query and each database molecule, it cannot be combined with prefiltering methods and uses exponential time for each traversed vertex or node, respectively, of the subgraph tree.

Messmer, Shearer, Bunke and Venkatesh introduced a decision tree for the computation of subgraph- and maximum common subgraph isomorphisms of object-graphs derived from video images against a database of model graphs (see B. T. Messmer and H. Bunke, Pattern Recognition, 32(12):1979-1998, 1999 and K. Shearer, H. Bunke, and S. Venkatesh, Pattern Recognition, 34(5):1075-1091, 2001). The approach stores in a preprocessing step the complete isomorphism classes of all model graphs in a decision tree. An asymmetric graph with n vertices has n! (n factorial) isomorphic representations. The size of graphs to be stored and searched in the decision tree is limited to 12 vertices using current hardware and will never exceed 14 in the foreseeable future.

Borgelt, Meinl and Berthold (see C. Borgelt, T. Meinl, and M. R. Berthold, "MoSS: A program for molecular substructure mining" in Workshop Open Source Data Mining Software—2005, OSDM, pages 6-15, 2005; C. Borgelt, "Combining ring extensions and canonical form pruning" in Workshop on Mining and Learning with Graphs—2006, MGL, 2006) introduced in the field of frequent subgraph mining an algorithm for the computation of a subgraph tree containing canonic representatives of all subgraphs that have a given minimal support in a set of molecules. The algorithm is used for mining subgraphs that are correlated with molecular properties. Activity against a given target is such a property.

Bit-vector based screening methods are fast, but applied to a database that contains millions of compounds a single screening run takes several minutes. Therefore the methods cannot be used interactively and the results are hard to interpret.

None of the discussed methods computes the substructure space of a given set of molecules. The algorithms compute a set of molecules similar to a given query without further structuring the result. An extension of the result set can only be done by a complete recomputation. All discussed approaches for the computation of maximum common subgraphs in the 1-to-n case cannot be easily extended to edit-distances or general topological transformations or the m-to-n case where multiple query molecules are searched simultaneously.

It has now been found that the presented method according to the invention allows for the virtual screening of millions of druglike molecules within a second.

BRIEF SUMMARY OF THE INVENTION

In one aspect, the present invention relates to a topological index of a given set of molecules represented by colored graphs (input set) in form of a directed acyclic graph (tDAG), which contains all topologically different, connected, uncolored substructures of the given input set, wherein the uncolored graphs are the vertices (or nodes, respectively) of the tDAG and two vertices of the tDAG are connected, when the graph represented by the head vertex can be derived from the graph represented by the tail vertex by a primitive structural transformation.

In another aspect, the present invention relates to a directed acyclic graph of maximal common substructures (mDAG) of a given set of molecules, wherein the vertices are colored graphs, wherein all molecules to be screened and the query molecules are contained as vertices within the mDAG and wherein for each pair of molecules to be screened and the query molecules the mDAG contains directed paths such that the molecules are connected with their respective set of maximal common substructures.

Preferably, a weighting schema is applied to the directed acyclic graph of maximal common substructures to determine the maximum weight common substructures.

In a further aspect, the present invention relates to a method of computing a directed acyclic graph of maximum common substructures (mDAG) of a given set of molecules, for use in searching molecules among a number of molecules to be screened that are similar to a given set of query molecules, wherein the given set of molecules contains the molecules to be screened and the query molecules, wherein each molecule to be screened and each query molecule forms a vertex in the directed acyclic graph, the method comprising the steps of:
a) determining for each pair of molecules of the given set of molecules a maximum common substructure forming vertices of the directed acyclic graph; and
b) connecting each of the molecules with its respective maximum common substructure forming paths of the directed acyclic graph.

Preferably, steps a) and b) are preceded by steps:
a1) creating a vertex of the mDAG for each molecule to be screened and for each of the query molecules containing a colored graph of the molecule, except for molecules, for which an identical vertex already exists;
a2) sorting the vertices into levels of the mDAG according to the number of edges in the graph of the vertex, or any other mean such that the tail vertices of all edges of the mDAG are assigned to higher levels of the mDAG than the head vertices;
a3) creating subgraphs for every vertex by performing primitive structural transformations starting from the highest level, wherein the edges of the mDAG denote said primitive structural transformations which transform the graphs of the tail vertices into the graphs of the head vertices;
a4) moving to the next lower level and repeating step a3) until the lowest level vertices, representing subgraphs consisting of one atom only, are reached.

In the method of computing a directed acyclic graph of maximum common substructures (mDAG), preferably, a subgraph-based similarity measure is used for determining the maximum common substructure.

Preferably, a weighting schema is used for determining the maximum weight common substructure in the method of computing a directed acyclic graph of maximum common substructures (mDAG). Preferably, the mDAG is computed from a precomputed tDAG.

In another aspect, the present invention relates to a method for searching molecules among a number of molecules to be screened that are similar to a given set of query molecules, comprising the steps of:
a) providing a directed acyclic graph of maximum common substructures (mDAG) of a given set of molecules;
b) providing, for each query molecule, a data set comprising the query molecule, a molecule to be screened locally located in the directed acyclic graph, and their respective maximum common substructure.

Preferably the data set is created by walking zero, one or several steps up the path from the query molecule to a substructure and zero, one or several steps down the path to one of the molecules to be screened.

Preferably, the data sets are outputted ordered by decreasing similarity.

Preferably, the search terminates if
i) the complete directed acyclic graph is traversed;
ii) a given minimum similarity is reached;
iii) a given maximal number of requested results is returned.

Preferably, in step a) of the method for searching molecules a weighting schema is applied for providing a directed acyclic graph of maximum weight common substructures of a given set of molecules.

Preferably, in step a) of the method for searching molecules an mDAG is provided.

In the method for searching molecules, preferably, one molecule together with its neighbors within the mDAG is visualized, such that the chemical space of the set of molecules can be interactively traversed by repeatedly selecting a molecule neighboring the currently selected molecule, followed by visualization of the newly selected molecule together with its neighbors.

Preferably, for large molecules, steps a) and b) of the method for searching molecules are preceded by a fragmentation step, wherein each of the query molecules and the molecules to be screened are fragmented into overlapping fragments, and steps a) and b) are succeeded by a combination step, wherein the fragments are combined.

DETAILED DESCRIPTION OF THE INVENTION

The used similarity measure can be subgraph-based, edit-distance-based, general topological-transformation-based or a combination of these approaches.

Figure 1:
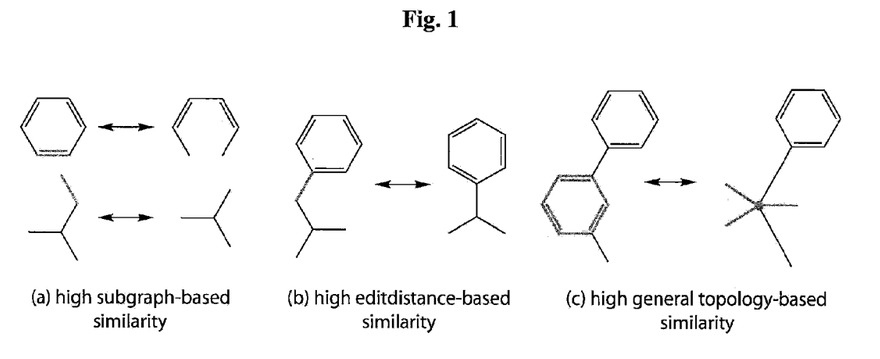
FIG. 1. exemplifies several structure-based similarity measures.

FIG. 1 shows examples of similar molecules using similarity measures based on different structural transformations. A high subgraph-based similarity between two molecules implies that a large maximum common subgraph can be reached by removing a small number of edges (see FIG. 1a). A high edit-distance similarity between two molecules implies that a large maximum common substructure can be reached by removing edges and merging the vertices adjacent to the removed edges (see FIG. 1b). A high general topology-based similarity between two molecules implies that a large common substructure can be reached by a small number of general structural transformations. FIG. 1c shows a general structural transformation where a ring is transformed into a star (ring-to-star-transformation).

The structural transformations used by subgraph-based and edit-distance-based similarity measures can be considered as special cases of general structural transformations. In general every kind of transformation is allowed, as long as the transformed structures and thereby the maximum common substructures are smaller or equal to the compared molecules.

In the following, we use the term primitive structural transformation for any type of single structural transformation, like the removal of an edge, or a ring-to-star-transformation. Similarly, we use the terms subgraph transformation, edit-distance transformation, and general topology-based transformation for specific types of single structural transformations.

Analog we use the term substructure for a graph derived by a primitive structural transformation from a given superstructure; and similarly the term subgraph for a graph derived by a subgraph transformation from a given supergraph.

Figure 2:
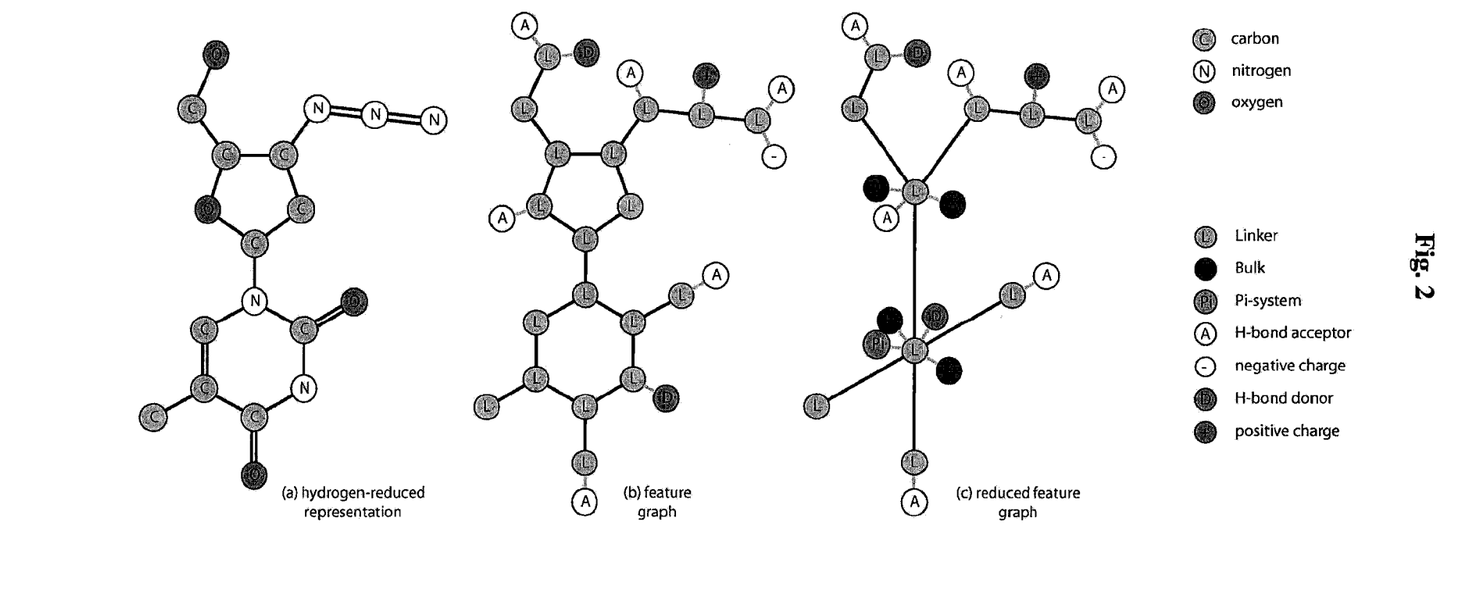
FIG. 2. shows possible representations of the HIV-drug zidovudine.

The presented method allows for different protonation states and representations of a molecule. FIG. 2 shows, as an example, three different representations of the HIV-drug zidovudine. FIG. 2a shows zidovudine as a hydrogen reduced graph. The FIGS. 2b and 2c represent zidovudine as a property graph (or feature graph, respectively) and a reduced property graph. While basically every graphical representation of a molecule can be used by the method, the property graphs are especially well suited. The linker vertices (L) of a property graph represent the topology of the represented molecule. The property vertices (A, D, ...) represent the physico-chemical properties of the adjacent linker vertices. This allows for a matching of topologically similar molecules, which differ by their composition of hetero-atoms using a subgraph-based similarity measure: like benzol, pyridine and pyrazine. By using general topological transformations molecules within one representation can be transformed stepwise into other representations. The property graph representation of zidovudine can be transformed into its reduced property graph representation by two ring-to-star-transformations.

The presented method compares two molecules by the size of their maximum common substructures. If one or both molecules are represented by multiple protonation states and/or representations, the most similar pair of representations is chosen. The maximum common substructure approach can be generalized to a maximum weight common substructure approach by the introduction of a positive weighting-schema. By using a weighting schema the influence of differently colored vertices or edges on the result can be (re)balanced. A maximum weight common substructure is not necessarily a largest, but a highest weighted substructure according to the weighting schema.

Figure 3:
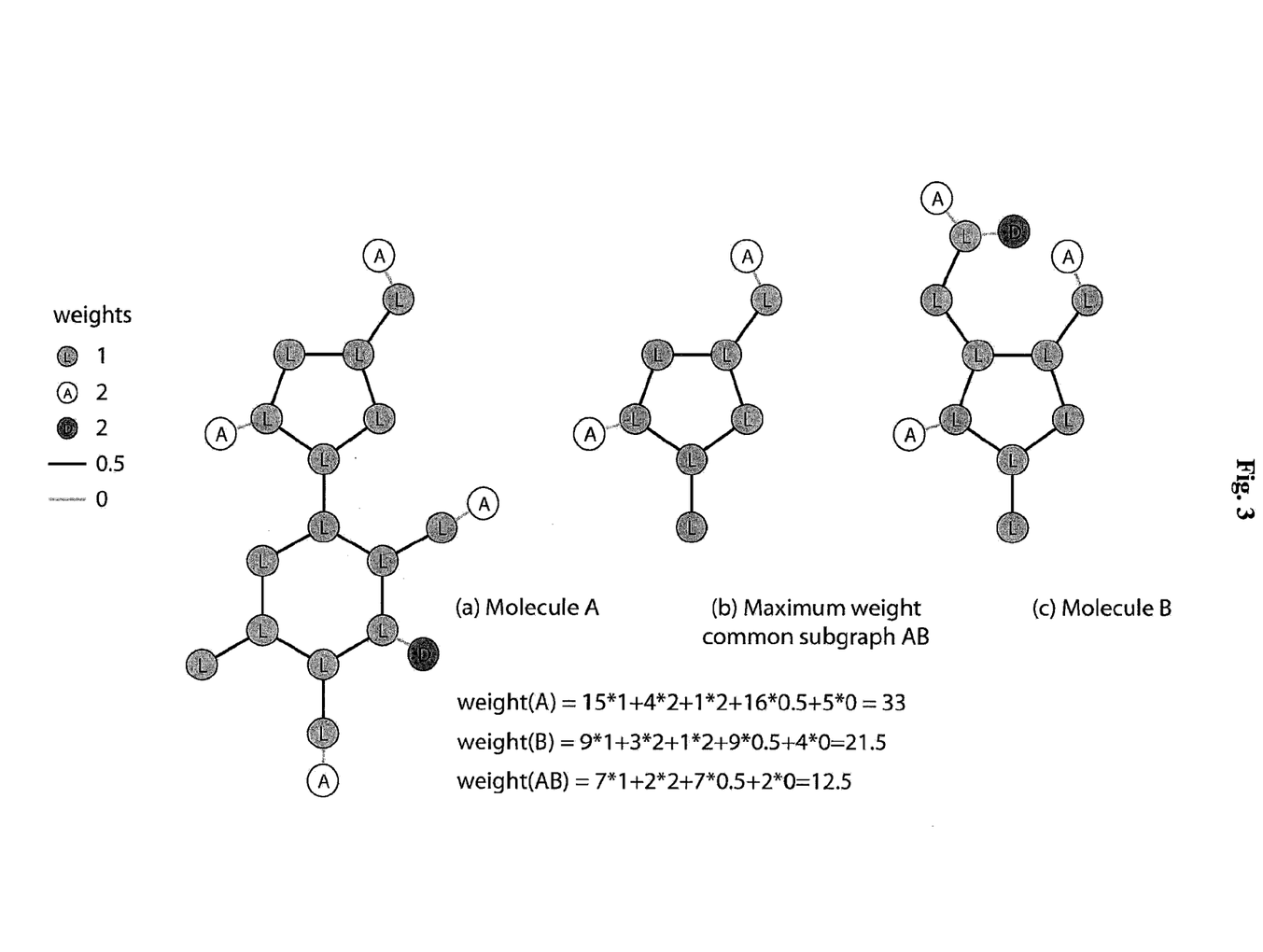
FIG. 3. shows a triple of two molecules and their maximum weight common substructure.

FIG. 3 shows an example for the calculation of the weight of two molecules A and B and their maximum weight common substructure AB. The weights of the compared molecules, the weight of their respective maximum weight common substructures and (optionally) the weights of the unmatched substructures can be combined into the final similarity measure. A commonly used combination schema is the tanimoto coefficient: $sim_{tanimoto}(A,B)=weight(AB)/(weight(A)+weight(B)-weight(AB))$. The similarity of the two molecules A and B shown in FIG. 3 using the tanimoto coefficient is 0.29.

The underlying idea of the presented method is the use of structural similarities between the screened molecules, such that multiple comparisons of identical substructures in different molecules are avoided. In a preprocessing step an index structure, namely the mDAG, of the given set of molecules (input set) is computed. The input set has to contain both, the screened molecules and the active molecules used for the screening. The mDAG is a connected, directed acyclic graph (DAG). Directed acyclic graphs are known to the person skilled in the art of computer science and mathematics. A sink of a DAG is a vertex, which has only incoming, but no outgoing edges. The vertices of a mDAG are colored graphs. All molecules of the input set are represented by vertices of the mDAG. For every pair of molecules in the input set the mDAG contains pairs of directed paths, such that the vertices that represent the molecules in the mDAG are connected with the set vertices that represent their respective maximal common substructures. A maximal common substructure of a set of structures is a substructure of every single structure contained in the set, such that no true superstructure of the substructure exists that is a substructure of every single structure contained in the set, too. A maximum common substructure of a set of structures is a maximal common substructure of the set, having a maximum size among all maximal common substructures of the set. The weighting schema has not to be known during the construction of the mDAG. A prior knowledge of the weighting schema and a minimal similarity allows for a faster construction of a smaller targeted mDAG. A targeted mDAG contains only vertices for those maximal common substructures that can be maximum weight common substructures of a pair of molecules in the input set, having a similarity greater or equal to the minimal similarity. Targeted mDAGs are limited to weighting schemas that are similar to the one used during their construction.

Figure 4:
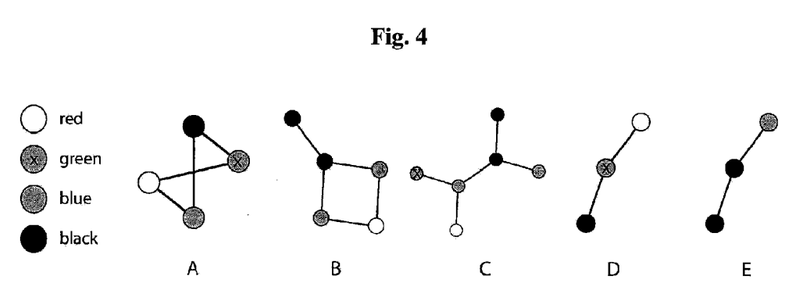
FIG. 4. shows a set of molecules represented by colored graphs {A,B,C,D,E}.

FIG. 4 shows a set of molecules represented by colored graphs; the different vertex colors represent discernable chemical groups (in the figures colors are represented by white, grey with a cross, grey and black).

Figure 5:
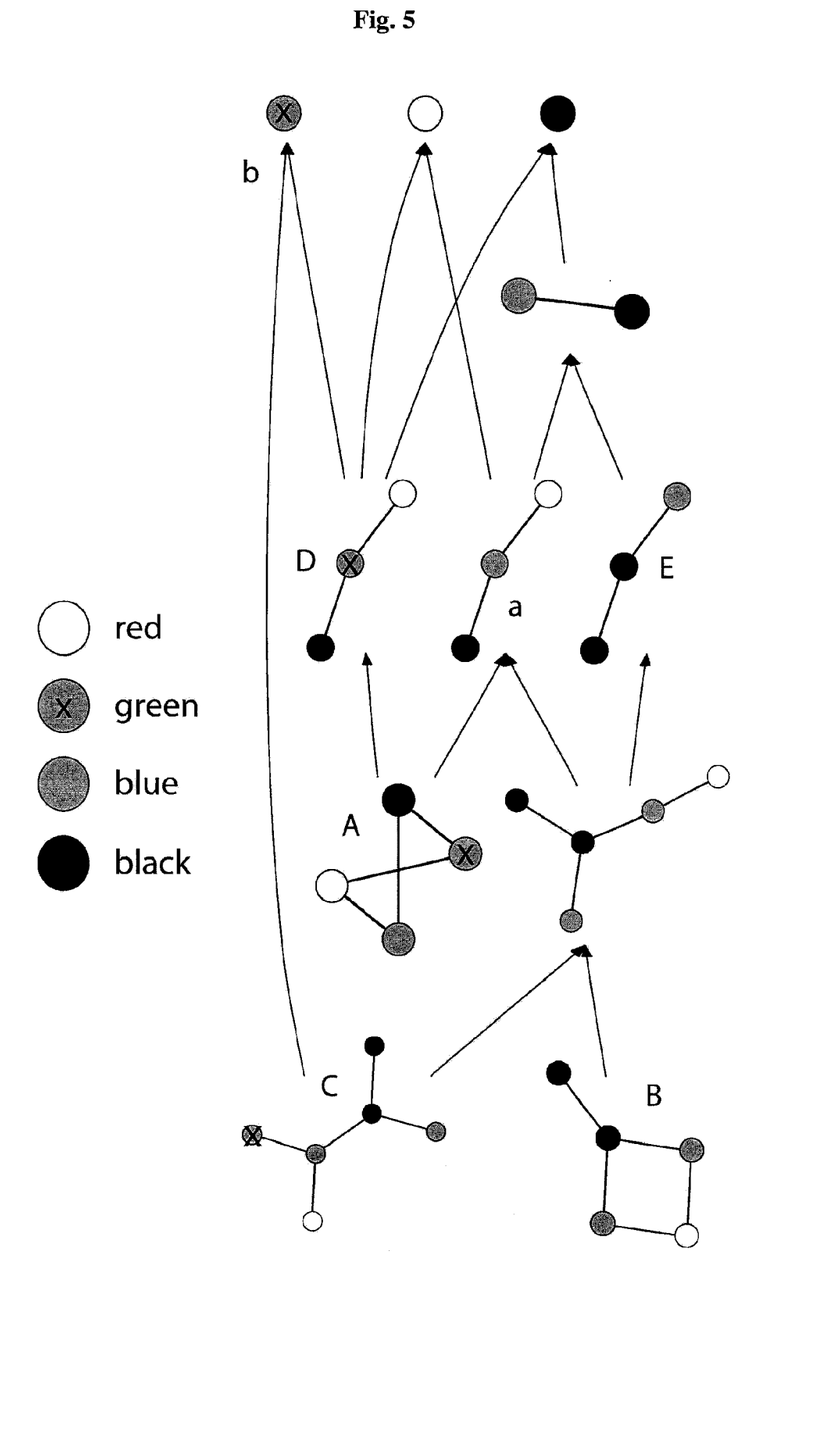
FIG. 5. shows the mDAG of {A,B,C,D,E}.

FIG. 5 shows the mDAG of {A,B,C,D,E} using a subgraph-based similarity measure. Depending on the weighting schema only two graphs can become the maximum weight common subgraph of A and C, the graphs a and b.

It is not necessary that the mDAG of a set of molecules represented by colored graphs can be computed interactively or that it is minimal, i.e. that it contains a minimum number of vertices and edges. For the use as an efficient index structure it is sufficient that it is possible to compute the mDAG for a large set of molecules and that it fits into the main memory of a computer to allow for fast searches. The mDAG of a set of two million druglike molecules, using a subgraph-based similarity measure, one protonation state per molecule and a reduced property graph representation, can be computed within a couple of days using a state of the art workstation. The resulting mDAG has a size in the order of 10 gigabytes.

The virtual screening for molecules similar to a given set of active molecules equals a local search within the precomputed mDAG. Starting from the vertices representing the active molecules, triples, each comprising an active molecule, a similar molecule and their respective maximum weight common substructure (cf. FIG. 3) are returned ordered by decreasing similarity. The search terminates, when the complete mDAG is traversed, a given minimum similarity is reached or a given maximal number of requested results is returned. The local search is similar to a breath first search (BFS) within an undirected version of the mDAG. However, in the presented method the BFS-algorithm is additionally constrained, by walking zero, one or several steps up a path from a vertex representing a query molecule to a vertex representing a substructure and zero, one or several steps down the path to a vertex representing one of the molecules to be screened.

Preferably, the mDAG can also be used for the visualization of the input set of molecules. Due to its size it is not possible to show the complete mDAG of a non-trivial set of molecules, but it is possible to visualize the graph of one molecule together with its neighbors within the mDAG, such that the chemical space of the set of molecules can be interactively traversed by repeatedly selecting the graph of a molecule neighboring the currently selected graph, followed by visualization of the newly selected graph together with its neighbors. In this way it is possible for the user to "scroll" through the mDAG and find molecules that are similar to the starting molecule, and might be active, without relying on similarities between the molecules that are computed using a global weighting schema.

By way of applying his knowledge and experience, the user might be able to find active molecules faster by "scrolling" than by analyzing molecules ordered by decreasing similarity.

The Computation of the mDAG

The mDAG of a given set of molecules represented as colored graphs (input set) and a given structure based similarity measure can be computed using a topological index, namely the tDAG, of the input set.

The tDAG is a connected DAG with a single sink. The vertices of the tDAG are uncolored graphs. Therefore, the tDAG does not contain information about the chemical or physical nature of the atoms or groups of the represented molecules. The tDAG of a given input set contains all topologically different (non-isomorphic), connected, uncolored substructures of the given set of colored graphs. The vertices of the tDAG contain links to the represented molecules of the input set. A vertex of the tDAG may contain links to several different molecules, which are topologically identical if the chemical nature of the atoms is disregarded. Depending on the chosen structure based similarity measure two vertices of the tDAG are connected, when the graph of the head vertex can be derived from the graph of the tail vertex by a primitive structural transformation, i.e. like the removal of an edge or a ring-to-star-transformation.

Figure 6:
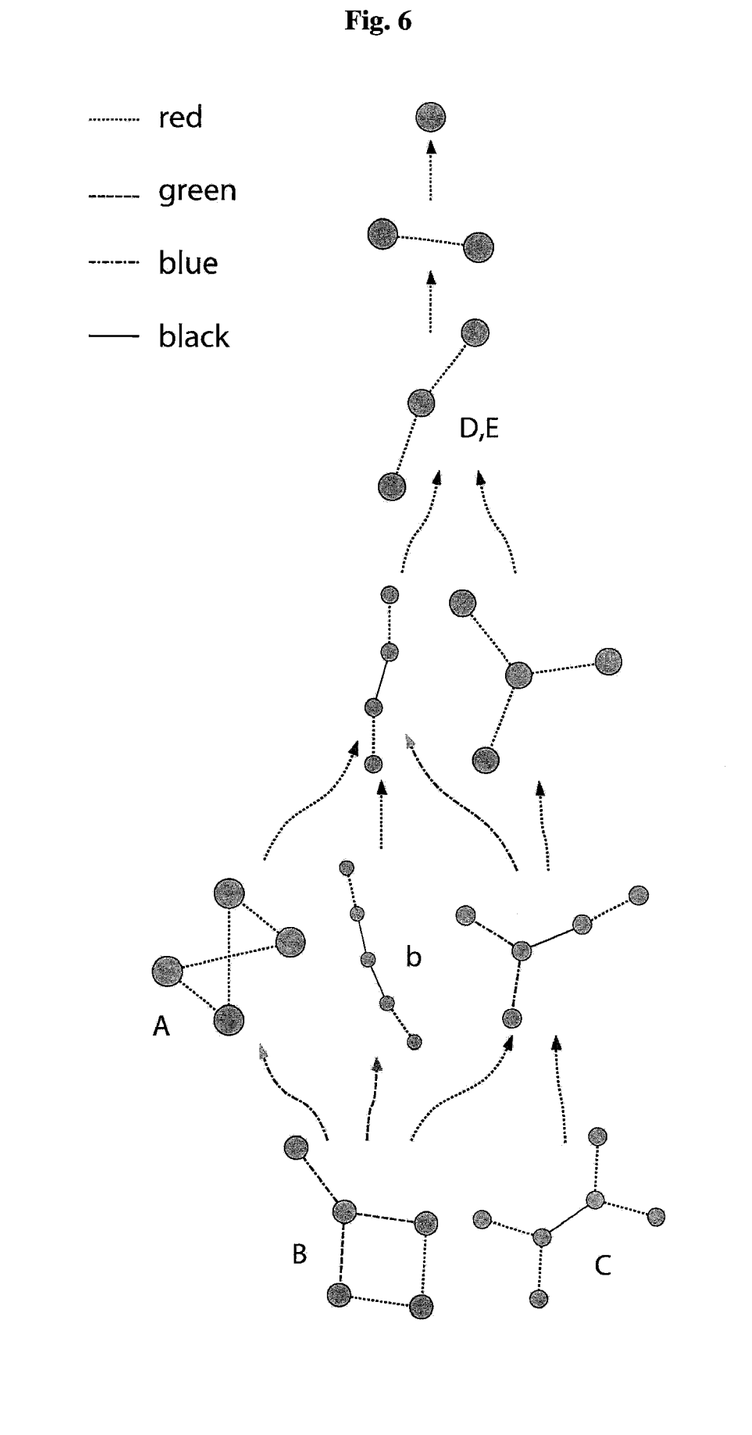
FIG. 6. shows the tDAG of {A,B,C,D,E}.

FIG. 6 shows the tDAG of {A,B,C,D,E} using a subgraph based similarity measure. The graphs contained within the tDAG are uncolored. The colors used in FIG. 6 are solely used to visualize equivalent structural transformations. By removing any of the green colored edges of the graph B the graph b is reached by the green edge of the tDAG starting at B. Together with the uncolored graph each vertex of the tDAG stores a set of generators of the corresponding permutation group. The permutation group is the group of possible symmetry operations, which, applied to the graph result in an identical graph.

The algorithm generates during the calculation of the mDAG the complete substructure space, called colored DAG, cDAG for short, of the given input set.

Figure 7:
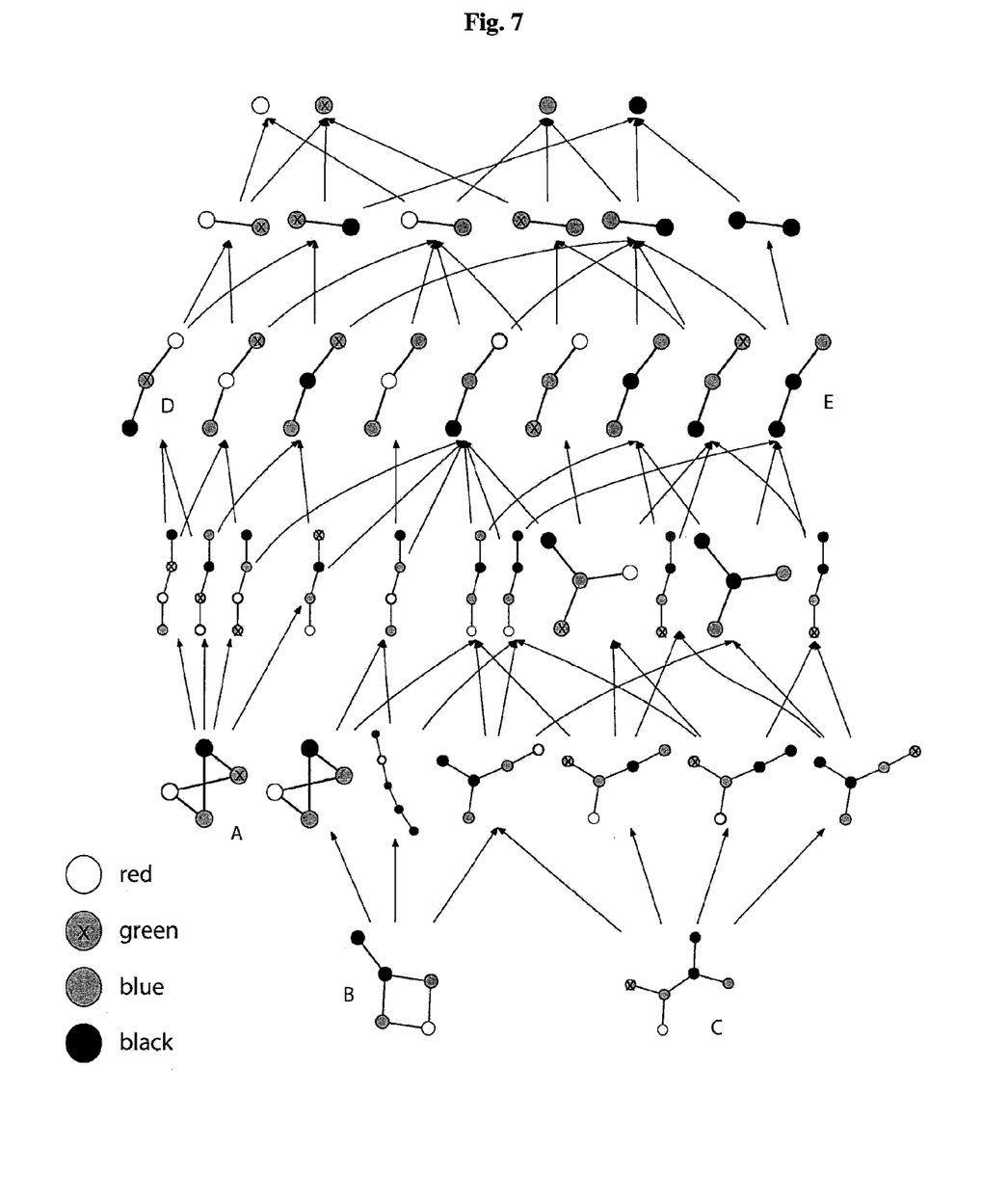
FIG. 7. shows the cDAG of {A,B,C,D,E}.

FIG. 7 shows the cDAG of {A,B,C,D,E} using a subgraph based similarity measure. The cDAG is very large. For a nontrivial set of molecules it is not possible to store the entire cDAG. An approximate setcover algorithm is used to limit the output of the algorithm to a coarse superset of a minimal size mDAG.

Initially the molecules of the input set, represented as colored graphs are assigned to the corresponding uncolored graphs of the tDAG. Then the algorithm calculates the mDAG level-by-level starting from the sources most distant from the sink(s) and ending at the sink(s) of the mDAG. Vertices of a DAG that have only outgoing and no incoming edges are sources. The levels of the DAG are assigned such that the tail vertices of all edges of the DAG are in a higher level than the head vertices. A sorting of the graphs according to their number of contained edges is sufficient in the presented case. For each level all colored graphs assigned to the same uncolored graph of the tDAG are processed together. First the generators of the permutation group of the uncolored graph are used to remove isomorphic colored graphs. Then the edges of the tDAG are used to derive and assign the substructures of the considered graphs to the next level. Finally the approximate setcover algorithm is used to decide for every vertex and every edge of the cDAG if it has to be added to the mDAG.

Figure 8:
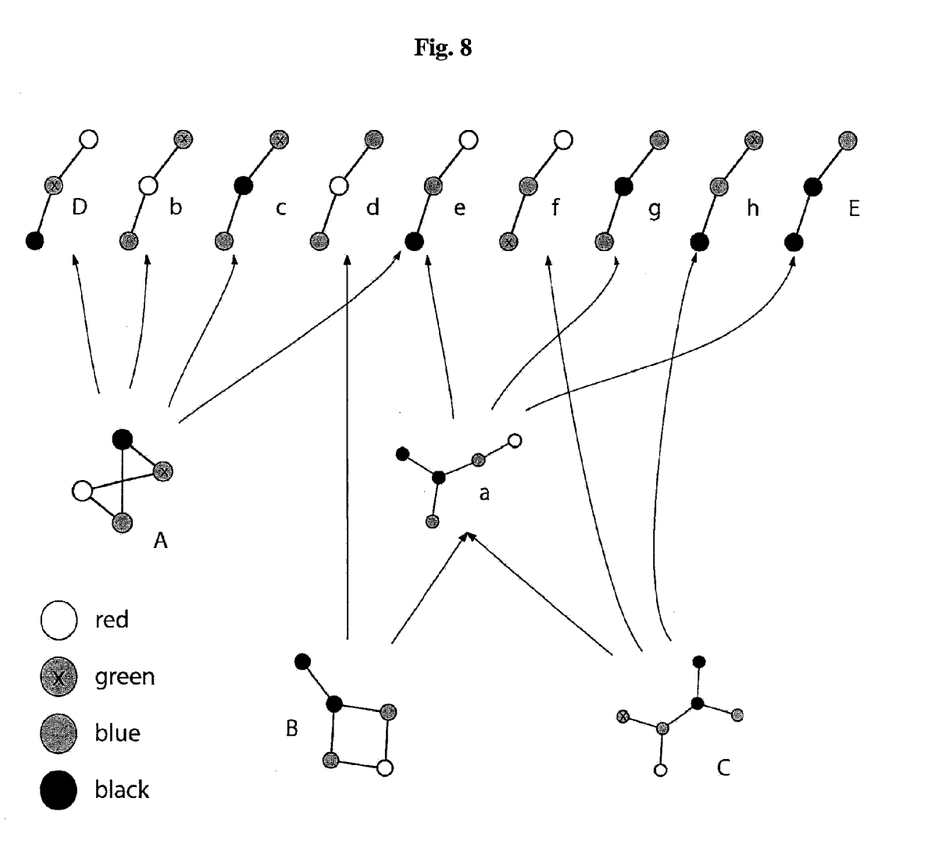
FIG. 8. shows a scheme for the computation of the mDAG of {A,B,C,D,E}.

FIG. 8 shows the state of the algorithm during the computation of the third level of the mDAG using a subgraph based similarity measure. The higher levels (four and five) of the mDAG are already computed. Nine differently (non-isomorphic) colored graphs {D,b,c,d,e,f,g,h,E} are considered. The graphs D and E belong to the input set; these graphs are always added to the mDAG. The graphs b,c,d,f,g and h have just one incident edge, therefore any pair of graphs, like B and C, which shares one of these graphs, in this case g, as a common subgraph, also shares its predecessor, a. For this reason the graph g can never become maximum common subgraph of B and C because there exists a larger common subgraph a, which is a maximum common subgraph of B and C. Accordingly, graph g can be omitted from the mDAG. The graph e has two incident edges. One from A the other from a. By the first edge the input graph A can be reached, by the second edge the input graphs B and C. Therefore e can become a maximum weight common subgraph of the graph pairs A,B and A,C. Thus, the graph e has to be added to the mDAG.

The algorithm can be stated as a classical setcover problem. Let X be the set of all vertices of the tDAG that correspond to colored graphs contained in the input set and that are reachable from the vertex under consideration. Let {X1, X2, ..., Xn} be the set of sets of vertices that are reachable from the considered vertex by traversing the first, second, ..., last incoming edge. Find a minimal size subset of {X1, X2, ..., Xn} whose union contains all elements of X. For the solution of the problem any approximate or exact setcover algorithm can be used (see T. H. Cormen, C. E. Leiserson, and R. L. Rivest, "Introduction to Algorithms", McGraw-Hill, pages 974-978, 1990). If a single set Xi is sufficient to cover X the considered vertex is omitted from the mDAG. Otherwise the vertex, together with those edges that correspond to elements of the covering set, is added to the mDAG. In the case of the vertex e the set X equals {A,B,C} and the sets X1 and X2 equal {A} and {B,C}.

Instead of storing the reachable subset of the input set within every tDAG vertex it is much more space efficient to compute the sets whenever necessary by traversing the already computed part of the tDAG.

The algorithm stores the unfinished levels using, for example, external memory such as a hard disc. Within a given level, first all contained, colored graphs are sorted by their corresponding uncolored graphs in external memory. Then at a time only those colored graphs that correspond to a single uncolored graph (a vertex of the tDAG) are loaded.

The size of the computed substructure space can be further reduced by the computation of a targeted mDAG. A targeted mDAG is computed like a normal mDAG, but together with the input set of colored graphs a weighting schema and a minimum similarity is given. This weighting schema is used to prune substructures where no pair of input graphs exists, such that: 1) The substructure is a minimum weight substructure of the given pair of graphs, and 2) the similarity between the pair of graphs is higher than the given minimum similarity.

An Improved Version of the Setcover Algorithm

Instead of computing the sets X1, X2, ..., Xn corresponding to the incoming edges of a considered vertex n directly, it is possible to first traverse the already constructed part of the tDAG reachable from n in a breath-first search (BFS) fashion and to compute for each traversed vertex m the reachable subset of ingoing edges to n. A computed subset is output whenever the traversed vertex m corresponds to an element of the input set. Finally the sets X1, X2, ..., Xn are constructed from the output and the algorithm continues as before.

The advantage of the improved version of the algorithm is that it can be stopped at any time. When the algorithm is stopped, the vertices that are still contained in the BFS-queue are added to the output, irrespective if they correspond to input molecules or not. The derived setcover is a superset of the setcover derived after the normal termination of the BFS-algorithm.

Another advantage is that it is not necessary to add sets to the output, which are covered by other sets that were written to the output before. This allows for an early termination of the BFS-algorithm, whenever all sets corresponding to the vertices contained in the BFS-queue are covered.

The Computation of the tDAG

One way to compute the tDAG of a given set of molecules represented by colored graphs (input set) and a given structure based similarity measure is by using a program that computes for a given uncolored graph a canonical code. The program nauty (see B. D. McKay, "Practical Graph Isomorphism" Congr. Numer., volume 30, pages 45-87, 1981) is an example for such a kind of program. A canonical code of a graph is a number that is assigned to the given graph by means of a canonization procedure; like the procedure implemented within the program nauty. The canonization procedure guaranties that any pair of isomorphic graphs is assigned the same canonical code and that any pair of non-isomorphic graphs is assigned a pair of non-identical codes.

The algorithm for the computation of the tDAG uses a lookup table that maps the canonical codes of the graphs currently contained in the tDAG to the vertices of the tDAG itself. For every molecule that has to be included into the tDAG first the corresponding uncolored graph is derived. Then the canonic code of the uncolored graph is computed. If the code is already present within the table the molecule is assigned to the corresponding vertex of the tDAG and the computation proceeds with the next molecule. Otherwise the uncolored graph is inserted into the tDAG, the molecule is assigned to the new vertex and the new vertex together with the corresponding canonic code is inserted into the table. Then recursively the substructures of the uncolored graph are derived by application of the given set of primitive structural transformations and inserted into the tDAG. Upon termination of every recursive call, the vertex of the substructure is connected with the vertex of its direct superstructure. Together with the canonic code, the program nauty also computes a generating set of the permutation group of the given graph. This set is needed for the computation of the mDAG and stored in the inserted vertices too.

The described procedure can in principle also be applied for the direct computation of the cDAG and thereby for the computation of the mDAG. However for a non-trivial set of input molecules the cDAG and the required lookup table do not fit into the memory of a computer, which means that the large amount of random access operations required by the algorithm have to be done using external memory. This renders the algorithm useless for the computation of the mDAG.

Besides the described procedure several other algorithms exist that can be used to compute the uncolored graphs corresponding to the vertices of the tDAG. The new idea about the computation of the tDAG is to store the graphs together with the connecting edges and to compute the tDAG at all, instead of computing the cDAG, which is too large to be used directly. The computation of the tDAG essentially splits the problem into a pure topological part that is solved by the tDAG and a colored part, which is addressed by the computation of the mDAG.

Extension to Larger Molecules

Due to the exponential growth of the size of the chemical space in the size of the contained molecules, the presented method is limited to molecules represented by colored graphs having less than 35 edges. In order to process larger molecules a fragmentation, search and combine strategy can be used. Instead of indexing complete molecules, for each molecule a set of overlapping fragments is stored. During the search a set of query fragments is used instead of the complete query molecule. Finally maximum common substructure matches of fragments, which correspond to the same result molecule, are combined into an approximate maximum common substructure match of the complete query and the complete result molecule.

Figure 9:
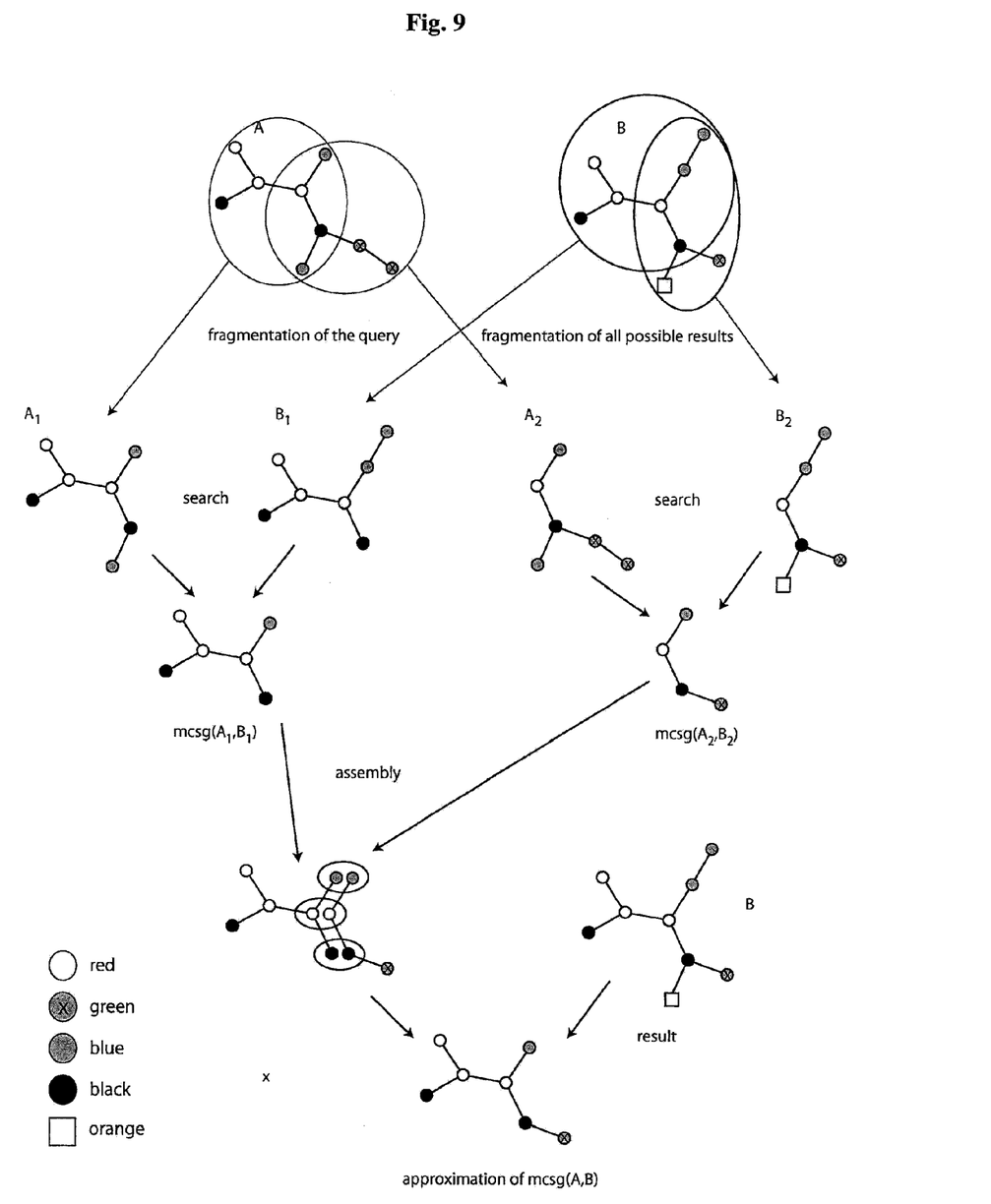
FIG. 9. shows a scheme for the Fragmentation, Search and Combine strategy.

FIG. 9 shows an example for the application of the fragmentation, search and combine strategy for the query molecule A and the result molecule B using a subgraph based similarity measure. In FIG. 9, the function mcsg(A,B) provides the maximum common subgraph of A and B.

The fragmentation, search and combine strategy relies on the capability of the search procedure to retrieve large and therefore significant matching fragments in very short time, which is facilitated by the present invention.

Example

Comparison to Other Virtual Screening Methods

Virtual screening methods are assessed by retrospective application to molecules of known activity. For this purpose, first a query (query molecule) is selected from a small set of molecules that are active versus the same target (active molecules). The remaining active molecules are mixed with a larger set of inactive molecules (other molecules). Then the virtual screening method is used, to sort the mixed set of all molecules by descending similarity versus the selected query molecule.

A commonly used measure for assessing the ability of a screening method to separate active molecules from inactive molecules is the enrichment factor (ef). The enrichment factor is defined for every initial fraction of the sorted list of molecules, as the number of active molecules contained within the initial fraction divided by the number of active molecules expected to be contained in the initial fraction by random. Because the enrichment factor is defined for every initial fraction of the set of all molecules, its values can be plotted as a curve, namely the enrichment curve. In the following, we first introduce a dataset. This dataset, split into subsets used for training and testing, is used by all subsequent calculations.

Then we train the weighting schema of the presented method using a genetic algorithm. Note that the weighting schema depends on the used molecular representation. We derive two sets of weighting schemas: one for property graphs, and one for reduced property graphs.

Finally, we compare the virtual screening results of the presented method with the screening results of two other, well-known virtual screening methods, namely FTrees (M. Rarey, J. S. Dixon, "Feature trees: A new molecular similarity measure based on tree matching", J Comput Aided Mol Des, 12:471-490, 1998), and MACCS Keys (MDL Information System Inc.).

Datasets

We selected 28 sets of active molecules, and 2 sets of (putatively) inactive molecules (other molecules). From every set of active molecules we randomly chose 3 query molecules.

Figure 10:
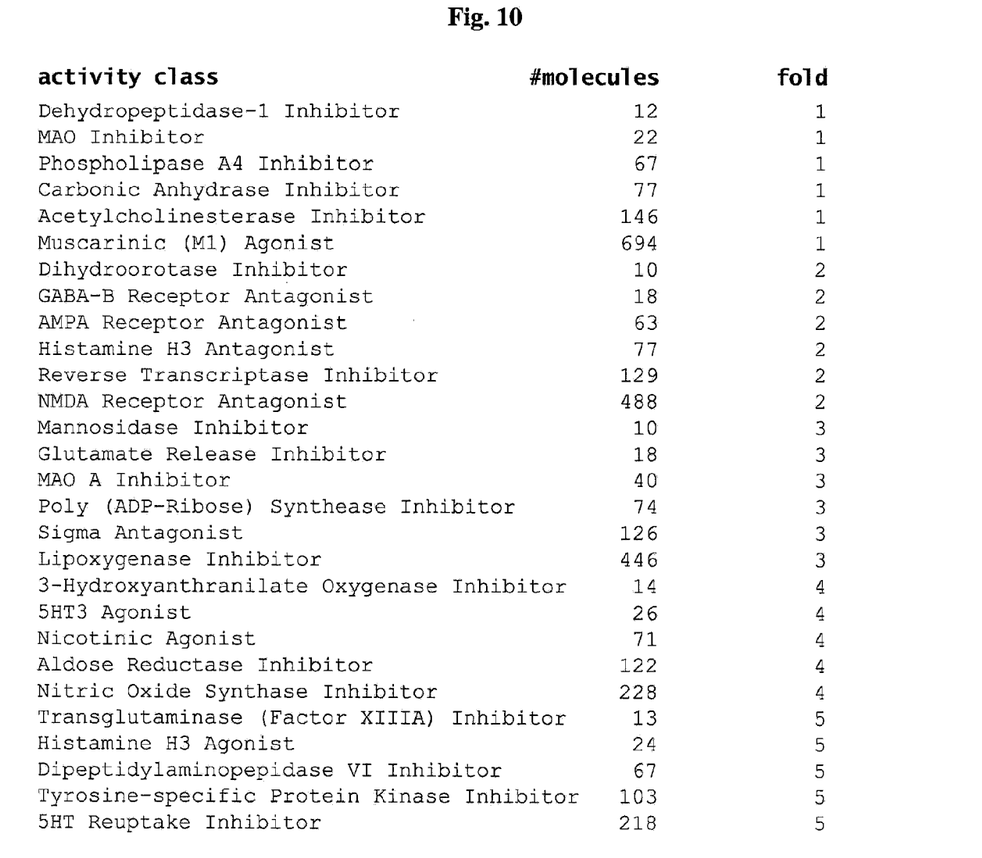
FIG. 10. lists the sets of active molecules used training, testing, and comparing the virtual screening methods.

All molecules are selected, such that their colored graph representations contain at most 25 edges. The active molecules are derived from the MDL Drug Data Report (MDDR). Every set of active molecules contains at least 10 molecules. The sets of active molecules are split into 5 sets, called folds (see FIG. 10). We use the different folds for training and testing our method in a 5-fold cross-validation setting.

The two sets of other molecules are derived from leadlike80 subset of the database ZINC (J. J. Irwin, B. K. Shoichet, "ZINC—A Free Database of Commercially Available Compounds for Virtual Screening.", J Chem Inf Model, 45:177-182, 2005). Both sets of other molecules comprise 23 k molecules. We use the first set for training, and the second set for testing.

Training

We trained the weighting schema of our method in a cross-validation setting using a genetic algorithm. The training of the weighting schemas for the two different types of molecular representations, namely property graphs and reduced property graphs, are independent. The subsequently presented training schema was applied twice, once for each representation.

Training in a 5-fold cross-validation setting means, 5 different optimizations are done. For every optimization a different fold of active molecule sets is set aside. The remaining 4 folds of active molecules, together with their respective sets of selected query molecules, and the training set of other molecules are used in training run. The value that is maximized by the genetic algorithm in every training run is the mean area under the first 10% of the enrichment curve. The mean is calculated over all queries and over all sets of actives contained in the respective folds.

Alter the termination of the genetic algorithm, the optimized weighting schema is applied to the excluded fold of active molecules, together with their respective sets of selected query molecules, and the testing set of other molecules. Because this testing run is done for every fold, results are derived for every set of active molecules. In the next section, the results derived from the testing runs are compared to the results obtained by using the other methods.

Comparison

Figure 11:
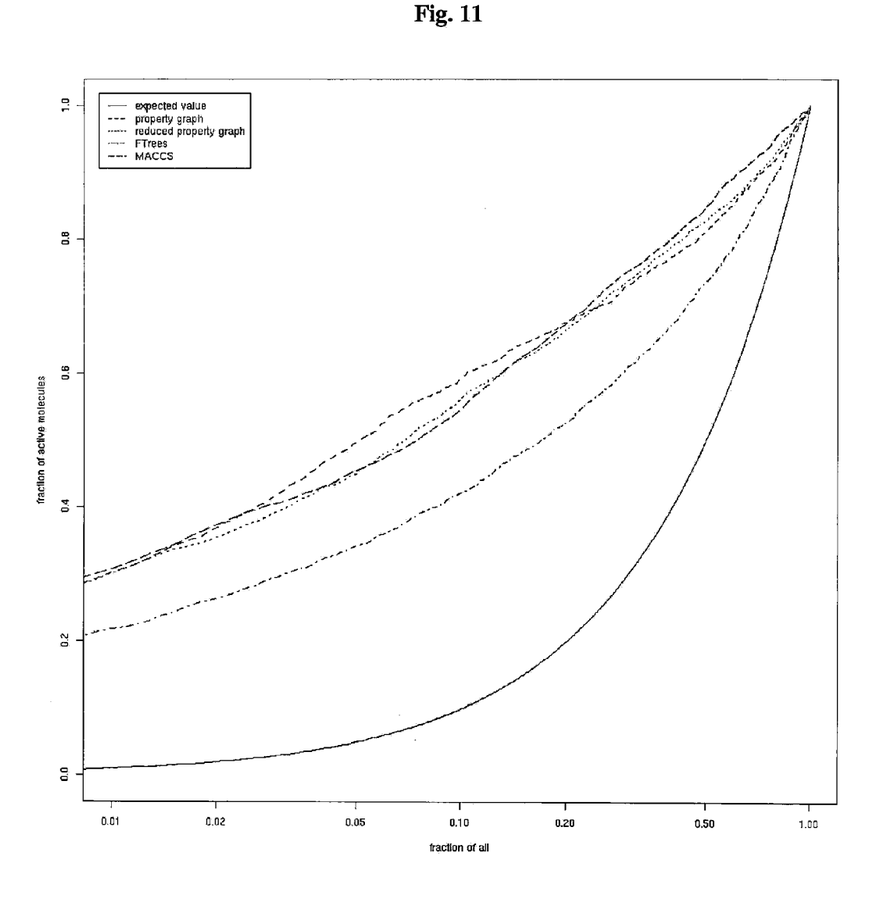
FIG. 11. shows the mean fraction of active molecules found, as a function of the initial fraction of the set of all molecules.

In this paragraph the results obtained by the testing runs of the presented method, using both: a property graph and a reduced property graph representation are compared to the results derived by using the virtual screening methods FTrees and MACCS. Note that for every method 28*3=84 identical virtual screening calculations are done. FIG. 11 shows a plot of the average fraction of active molecules found by each of the methods as a function of the initial fraction of the set of all molecules. The x-axis of the plot uses a logarithmic scale in order to ease the analysis of the most important, the initial part, of the plot. The curves of the presented method using reduced property graphs and the method MACCS are almost identical. The presented method using property graphs is slightly above the curves of the already mentioned methods up to a fraction of 0.2 of the set of all molecules; above 0.2 it is below. The curve of the method FTrees is always below the curves of all the other methods.

The plot does not allow for any conclusion concerning the significance of the observed results. A simple use of error bars for each curve does not lead to the desired result, because the enrichment factors obtained by all methods are highly dependent on the sets of actives. Thus the variance over the different sets of actives is mixed up with the variance of the different methods. However, sets of actives that are difficult for one method are usually difficult for the other methods, too.

Figure 12:
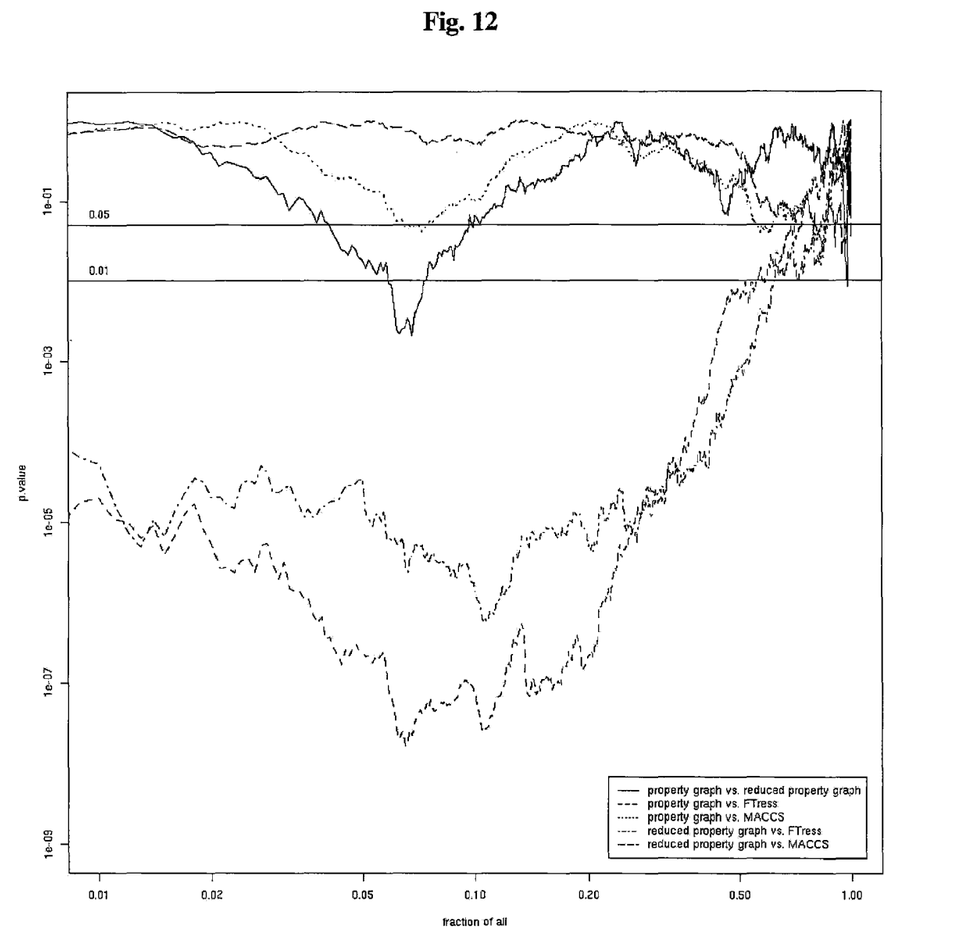
FIG. 12. shows the significances of the results presented in FIG. 11.

Every point on the plotted curve represents a mean over 84 single values. Because for every method the same calculations are done, for every fraction of all molecules 4 times 84 paired values are available. Thus the pairwise t-test can be used to assess the significance of the shown differences. FIG. 12 shows the results (p-values) of the paired t-tests. p-values below 5% are significant; below 1% are highly significant.

Thus it is highly significant that all methods outperform FTrees. Moreover, between 4% and 10% the property graph representation significantly outperforms the reduced property graph representation. All other differences between the compared means are insignificant.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. A computer-implemented method for searching molecules from among a number of molecules to be screened that are similar to a given set of query molecules, comprising the steps of:
    a) accessing data representing the molecules stored on a computer-readable medium;
    b) determining maximum common substructures of a given set of molecules based on the data representing the given set of molecules;
    c) generating a directed acyclic graph of the maximum common substructures (mDAG);
    d) generating, for each said query molecule, a data set comprising data representing the query molecule, data representing a molecule to be screened locally located in the directed acyclic graph, and data representing their respective maximum common substructure; and e) storing the data;

f) wherein all of the foregoing steps are performed using a computer.

2. The method of claim 1, wherein the data set is created by walking zero, one or several steps up the path from the query molecule to a substructure and zero, one or several steps down the path to one of the molecules to be screened.

3. The method of claim 1, wherein the data sets are calculated and outputted ordered by decreasing similarity.

4. The method of claim 1, wherein the search terminates if
   i) the complete directed acyclic graph is traversed;
   ii) a given minimum similarity is reached;
   iii) a given maximal number of requested results is returned.

5. The method of claim 1, wherein in steps b) and c), a weighting schema is applied for providing a directed acyclic graph of maximum weight common substructures of a given set of molecules (targeted mDAG).

6. A computer-implemented method for searching molecules from among a number of molecules to be screened that are similar to a given set of query molecules, comprising the steps of:
   a) accessing data representing the molecules stored on a computer-readable medium;
   b) determining maximum common substructures of a given set of molecules based on the data representing the given set of molecules;
   c) generating a directed acyclic graph of the maximum common substructures (mDAG);
   d) generating, for each said query molecule, a data set comprising data representing the query molecule, data representing a molecule to be screened locally located in the directed acyclic graph, and data representing their respective maximum common substructure; and
   e) storing the data,
   f) wherein all of the foregoing steps are performed using a computer,
   wherein in step c), a directed acyclic graph of the mDAG of a given set of molecules is provided, wherein the vertices are colored graphs, wherein all molecules to be screened and the query molecules are contained as vertices within the mDAG, wherein for each pair of molecules to be screened and the query molecules the mDAG contains paths such that the molecules are connected with their respective maximum common substructure, and wherein molecules are included using different protonation states and representations.

7. The method of claim 1, wherein one molecule together with its neighbors within the mDAG is visualized, such that the chemical space of the set of molecules can be interactively traversed by repeatedly selecting a molecule neighboring the currently selected molecule, followed by visualization of the newly selected molecule together with its neighbors.

8. The method of claim 1, wherein steps a), b), c), and d) are preceded by a fragmentation step, wherein each of the query molecules and the molecules to be screened are fragmented into overlapping fragments, and steps a), b), c), and d) are succeeded by a combination step, wherein the fragments are combined.

9. A computer-implemented method for searching molecules from among a number of molecules to be screened that are similar to a given set of query molecules, comprising the steps of:
   a) accessing data representing the molecules stored on a computer-readable medium;
   b) determining maximum common substructures of a given set of molecules based on the data representing the given set of molecules;
   c) generating a directed acyclic graph of the maximum common substructures (mDAG);
   d) generating, for each said query molecule, a data set comprising data representing the query molecule, data representing a molecule to be screened locally located in the directed acyclic graph, and data representing their respective maximum common substructure; and
   e) storing the data,
   f) wherein all of the foregoing steps are performed using a computer,
   wherein in step c), a directed acyclic graph of maximum common substructures (mDAG) of a given set of molecules is provided, wherein the vertices are colored graphs, wherein all molecules to be screened and the query molecules are contained as vertices within the mDAG, wherein for each pair of molecules to be screened and the query molecules the mDAG contains paths such that the molecules are connected with their respective maximum common substructure, and wherein a weighting schema is applied to determine the maximum weight common substructures (targeted mDAG).

* * * * *